United States Patent [19]

Drabs

[11] 4,262,806
[45] Apr. 21, 1981

[54] AUTOMATIC DETECTION AND REJECTION OF FOREIGN BODIES FROM VEGETABLES TRANSPORTED ON A CONVEYOR

[75] Inventor: Henri J. J. Drabs, Brabant, Belgium

[73] Assignee: Elbicon Electronics PVBA, Winksele-Herent, Belgium

[21] Appl. No.: 932,894

[22] Filed: Aug. 11, 1978

[30] Foreign Application Priority Data

Aug. 18, 1977 [BE] Belgium .............................. 857904

[51] Int. Cl.³ .............................................. B07C 5/342
[52] U.S. Cl. ..................................... 209/577; 209/587; 250/223 R; 356/51
[58] Field of Search ....................... 209/576, 577, 587; 250/214 A, 214 AG, 223 R; 356/51, 237

[56] References Cited

U.S. PATENT DOCUMENTS

| | | | |
|---|---|---|---|
| 3,097,743 | 7/1963 | Scholten et al. | 209/577 X |
| 3,382,975 | 5/1968 | Hoover | 209/580 X |
| 3,435,950 | 4/1969 | Suverkrop | 209/577 |
| 3,586,168 | 6/1971 | Osheff et al. | 209/576 X |
| 3,652,791 | 3/1972 | Shuey | 250/214 AG |
| 3,675,769 | 7/1972 | Story | 209/577 |
| 3,784,307 | 1/1974 | Jackson et al. | 356/51 |
| 3,797,943 | 3/1974 | Nagao et al. | 356/237 |
| 3,899,415 | 8/1975 | Codding et al. | 209/581 X |

Primary Examiner—Joseph J. Rolla
Attorney, Agent, or Firm—Alan H. Levine

[57] ABSTRACT

A device for detection and removal of foreign bodies from vegetables dispersed and transported on a conveyor belt consisting of a multichannel detection system based on reflection analysis of polarized infra-red light. The reflected light is amplified, filtered and applied to a delayed automatic gain control circuit (A.G.C.). The A.G.C. output is compared with a reference voltage window to control the ejection system.

10 Claims, 3 Drawing Figures

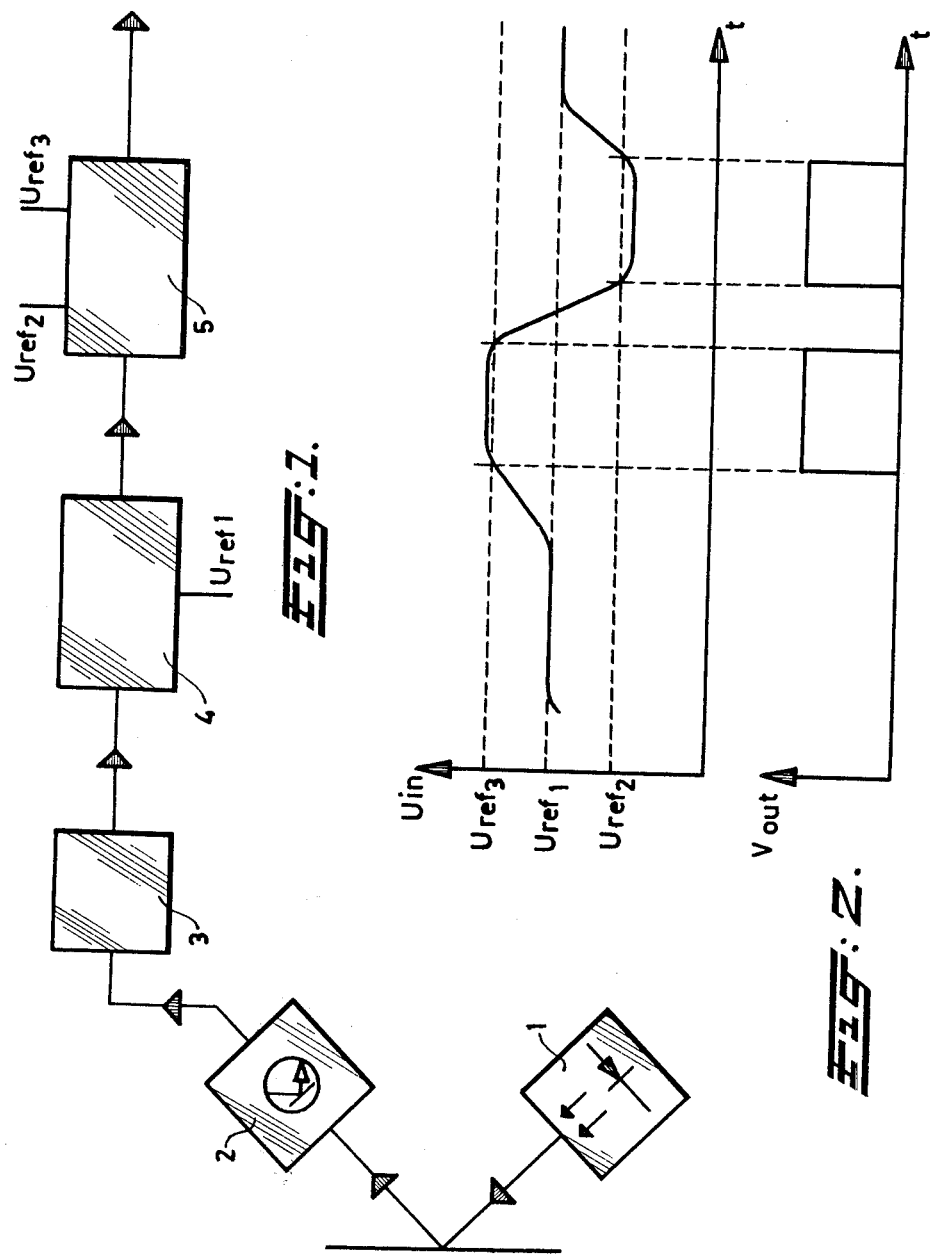

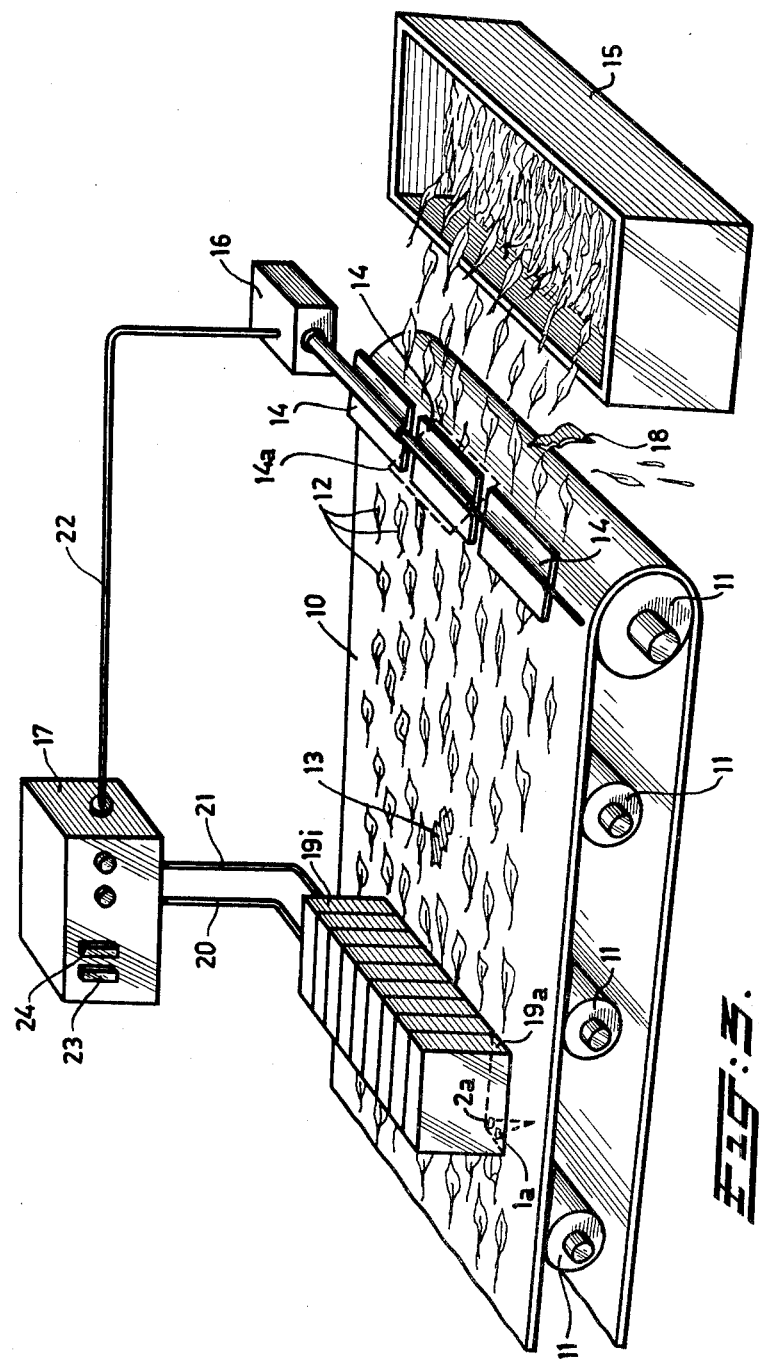

AUTOMATIC DETECTION AND REJECTION OF FOREIGN BODIES FROM VEGETABLES TRANSPORTED ON A CONVEYOR

My invention relates to the detection and removal of foreign bodies from vegetables dispersed and transported on a conveyor belt by a system consisting of a multichannel detection system based on reflection of polarised infra-red light, and mounted above the conveyor. Each channel consists of an infra-red modulated light source, synchronised with the sources of the other channels and combined with an infra-red receiver capable of detecting the reflected infra-red light. The output signal of the receiver is amplified and filtered and applied to a delayed automatic gain control circuit (A.G.C.) that tries to keep the output signal constantly on a predetermined first level. The output signal of the A.G.C. is applied to at least one comparator, providing at least one reference level adjustable for the total of all comparators giving an output signal at the moment that the output signal of the automatic gain control circuit exceeds the adjustable reference level of the comparators, such output signal being used to pilot an ejection system capable of removing the foreign objects from the good product.

SUMMARY OF THE INVENTION

In many cases, in canning or deep freezing industries the impurities between vegetables must be removed before the product is ready for treatment. An example is the automatic harvesting of vegetables, e.g., green beans, destined for preserves.

If often happens that foreign bodies such as rats, mice, rabbits pheasants or parts thereof, stones and sticks, etc are also collected and arrive at the sorting station. Until now undesired objects have been removed manually—an expensive and often fallible system. Indeed, it happens often that the above mentioned impurities are also canned.

No system has been found up to now to solve this serious problem well known by all manufacturers.

The present invention offers a genuinely revolutionary electronic detection system for automatic removal of impurities. The invention is based on the knowledge that objects of a different colour or a different structure have in general also a different reflection coefficient for infra-red rays. The principal of detection is based on the reflection of modulated infra-red light on the objects which are to be detected. That is to say that the electronic circuitry detects the difference between the reflection level of the vegetables and the reflection level of the unwanted objects. This naturally implies that the reflection of the conveyor belt must be chosen as close as Possible to the reflection of the vegetables.

In accordance with the invention the vegetables are transported on a conveyor, moving with high velocity (2.5 meters/second) A detection unit is mounted over the conveyor. At the end of such a conveyor an automatic ejection system is mounted. One way to do this is the use of electro-pneumatic ejectors. Each of these ejectors can be separately activated, this to reduce the loss of good product to a minimum.

In accordance with the invention the device is composed of a detection and a removal system of foreign bodies from vegetables dispersed and transported on a conveyor belt and consists of a multichannel detection system based on reflection of polarised infra-red light, and mounted above the conveyor. Each channel consists of an infra-red modulated light source, synchronised with the sources of the other channels and combined with an infra-red receiver capable of detecting the reflected infra-red light. The output signal of the receiver is amplified and filtered and applied to a delayed automatic gain control circuit (A.G.C.) that tries to keep the output signal constantly on a predetermined first level. The output signal of the A.G.C. is applied to at least one comparator, providing at least one reference level adjustable for the total of all comparators giving an output signal at the moment that the output signal of the automatic gain control circuit exceeds the adjustable reference level of the comparators, such output signal being used to pilot an ejection system capable of removing the foreign objects from the good product.

Preferably each comparator is provided with two different reference levels, one to fix the allowable upper limit of more reflection and the second to fix the allowable lower limit of less reflection. Furthermore, in a preferred embodiment of the invention the setting of these reference levels is common for all comparators and is done by thumbwheel switches via analog-digital convertors in 99 steps which results in a considerable sensitivity range, so that it is possible to adjust the sensitivity for objects reflecting less than the vegetables independently from the sensitivity for objects reflecting more than the vegetables. The system works very reliably under real industrial circumstances especially because of the use of an automatic gain control circuit (A.G.C.) per detection channel, which fully compensates for influence of temperature on certain components, aging of components ambient light, discolouration of detector lens, etc.

The system works well even with high belt speeds up to 2.5 meters/second which allows high capacity ratings, thereby increasing efficiency and control capacity. On a belt 800 mm wide througputs of 10 to 15 t.P.H. are possible with a vibrating feed to spread the product over the full belt width. Standard components are used for the construction of the electronic circuitry which make maintenance easy and keeps the price very reasonable.

DESCRIPTION OF THE DRAWINGS

FIGS. 1, 2 and 3 illustrate the invention

FIG. 1 is a block diagram of an embodiment in accordance with the invention;

FIG. 2 is a diagram of output levels to illustrate this embodiment; and

FIG. 3 shows schematically a complete installation in accordance with the invention.

DESCRIPTION OF PREFERRED EMBODIMENTS

FIG. 1 shows a embodiment of a detection unit (channel) used in the system in accordance with the invention. In practice the vegetables are transported on a conveyor—see FIG. 3—over which a detection system, composed of a certain number of detection units, is mounted laterally. Each detection unit consists of an infra-red transmitter 1, e.g., a light emitting diode, which is directed towards the conveyor belt, and the reflected rays are detected by an infra-red sensitive receiver 2, e.g., phototransistor connected in a circuit that gives an output signal proportional to the reflected infra-red light detected by the receiver. The reflection coefficient of the conveyor belt must be chosen as close as possible to the reflection coefficient of the vegetables to be sorted so that parts of the conveyor belt not covered with vegetables do not change the level of reflected infra-red rays detected by the receivers. However, foreign objects and impurities have in general a reflection coefficient for infra-red rays that is different from that of the conveyor belt or the treated vegetables. This means that the reflected light level received by the corresponding receivers will change when a foreign object passes on the conveyor belt underneath the detectors which will cause a change in the output signal of those receivers. These output signals are consequently an indication of the presence or the absence of foreign objects on the conveyor belt.

The output signal of each detector is applied to a filter-amplifier 3, the output of which, indicated as a detection signal, is applied to an automatic gain control circuit (AGC) 4. This circuit provides a constant output signal for slow changes of the input signal. Therefore this circuit continuously compares its output signal level with a fixed reference level, U ref 1 (FIG. 2). Quick changes in the input signal such as caused by a foreign body passing underneath the detectors, cannot be compensated for and will therefore appear at the output of this circuit, so that such output signal is different from Urefl. Each detection unit furthermore contains an electronic comparator 5. This comparator has at least one, but preferably two reference levels that fix the allowed reflection level limits and that compare continuously the output signal of the AGC network 4 with one or two independent reference levels, Uref 2 and U ref 3 (FIG. 2). The setting of these reference levels is common for all comparators and in the case of two reference levels, each comparator gives an output signal when the output signal of its corresponding AGC circuit exceeds the sensitivity setting upper limit U ref 3 or falls under the lower limit U ref 2 (FIG. 2). When two reference levels are used to for comparison with the level of the output signal of the AGC circuit, one double or two single comparators with a common output can be used. Indeed it is sufficient to know that a foreign object is detected and it is irrelevant to know whether the object is more reflective or less reflective than the treated vegetables. Consequently we may say that an output signal on a single or a double comparator indicates the presence of a foreign body and will be used for controlling an ejection system. FIG. 2 illustrates in the upper diagram the evolution of an input signal, U-in, on a double comparator at the moment that a foreign body that is more reflective (U ref 3) than the belt or the good product is sensed (U ref 1) followed by a foreign object that is less reflective than U ref 2.

The lower diagram shows the output signal of the comparator. The output signals of a group of comparators corresponding with a series of detectors that supervises a well defined portion of the conveyor belt are put in parallel and applied to an electronic circuit (not shown) such as a shift register, that shifts the information in order to obtain a delayed control of an ejection system mounted at the end of the conveyor. The ejection system physically corresponds with the above-mentioned group of detectors and is activated at the moment that the foreign body arrives at the end of the conveyor. This guarantees minimum loss of foodstuffs due to local selection of one of several ejection elements relative to the detected impurity. The shift register lengths are compressable as a function of belt speed and the physical distance between the detector units and the ejection system. As an ejection system for removing the foreign bodies, A series of electro-pneumatic flap doors controlled by the shift register outputs can be used, each flap being able to partially interrupt the foodstuff stream when it leaves the conveyor belt.

In accordance with the invention common adjustment facilities are possible for the entire group of detectors for:

a. the digital sensitivity setting for the maximum allowable reflection limit (plus reflection U ref 3) via an analog digital converter;

b. The digital sensitivity setting for the minimum allowable reflection limit (less reflection U ref 2) via an A-D convertor;

c. The digital setting of the length of the shift registers; and d. The digital setting of the minimum time that an ejection unit is energised, apart from the minimum time an ejection unit will be energised as a function of the physical length of the foreign object body.

FIG. 3 is a schematic representation of a complete installation in accordance with the invention. It consists of a conveyor belt 10 guided over rolls 11, on which the vegetables to be sorted 12 together with foreign objects 13 are transported. At the end of the conveyor a number of electric or pneumatic flap doors 14 is mounted. When these flap doors are in the position shown in solid lines in the drawing, then the objects on the belt will, due to the high belt speed, fly under the flap doors and arrive on a second conveyor or in a container 15. When however one of the flap doors, e.g., the centre flap is moved to the dotted line position 14a, which will be the case when the ejector mechanism 16 receives an ejection command from the control unit 17, then the object to be removed will bump against the flap door, together with a minimum of good product, and drop down just at the end of the conveyor 18, where foreign bodies arrive on a third conveyor or in a container (not shown).

Mounted over the conveyor belt are a number of detection units, one next to the other, each composed in the way as indicated in FIG. 1. They are indicated with reference numbers 19a ... 19i. Each detector 19a ... 19i is equipped with an infra-red transmitter 2a and an infra-red receiver 1b, as described with reference to FIG. 1.

All these elements operate as described with reference to FIG. 1, the reference levels being set for all detector units 19a ... 19i together from the central control unit 17, via the control connection 20. The respective output signals of the comparators are applied, via connection 21 to the central ejection unit assembly 17, which triggers the driving mechanism 16 that controls the flap doors 14. The reference levels are adjusted by means of thumbwheel digit-switches 23, 24.

The ejection information of a group of comparators of the individual detection channels is combined to control the command of one of the flap doors 14a–14c.

What is claimed is:

1. An apparatus for separating foreign bodies from vegetables being transported on a conveyor, the system comprising, (a) a transmitter for directing infra-red radiation at the conveyor, (b) a receiver for receiving the infra-red radiation reflected by the vegetables and foreign bodies being carried by the conveyor, the receiver producing an output signal proportional to the reflected infra-red radiation, so that the output signal corresponding to radiation reflected from a vegetable is different from the output signal corresponding to radiation reflected from a foreign body, (c) an automatic gain control circuit to which the output signal from the receiver is applied, the circuit producing a predetermined output signal in response to the output signal from the receiver corresponding to radiation reflected from a vegetable, said predetermined output signal remaining constant despite relatively slow changes in amplitude of the output signal from the receiver, and the circuit producing a different output signal in response to a relatively rapid change in the output signal from the receiver corresponding to radiation reflected from a foreign body, (d) comparator means for comparing the output signal from the automatic gain control circuit with at least one reference level, the comparator means producing no output signal in response to the predetermined output signal from the automatic gain control circuit, but the comparator means producing an output signal in response to a different output signal from the circuit having a level beyond the reference level, and (e) ejection means responsive to output signals from the comparator means for separating foreign bodies from the vegetables.

2. An apparatus as defined in claim 1 wherein the comparator means compares the output signal from the automatic gain control circuit with two reference levels, the reference levels being above and below, respectively, the predetermined output signal from the automatic gain control circuit, the comparator means producing no signal when it receives a signal from the circuit which is between the reference levels, but the comparator means producing an output signal in response to an output signal from the circuit which is either above the higher reference level or below the lower reference level.

3. An apparatus as defined in claim 1 wherein the infra-red radiation from the transmitter is modulated.

4. An apparatus as defined in claim 1 wherein the infra-red radiation from the transmitter is polarized.

5. An apparatus as defined in claim 1 including delay means between the comparator and ejection means for causing the ejection means to respond at an interval after the comparator produces a signal, during which time the conveyor carries the foreign body between the receiver and the ejection means.

6. An apparatus as defined in claim 5 wherein the delay means is a shift register.

7. An apparatus as defined in claim 1 wherein each transmitter and receiver comprises a detection unit having its own automatic gain control circuit and comparator means, and including a plurality of such units arranged crosswise of the conveyor, the reference levels of all the comparators being the same.

8. An apparatus as defined in claim 7 including common means for adjusting the reference levels of all the comparators.

9. An apparatus as defined in claim 7 including a plurality of ejection means arranged crosswise of the conveyor, each ejection means being aligned in the direction of travel of the conveyor with at least one of the detection units, and each ejection means being responsive to output signals only from the comparator associated with the detection unit with which that ejection means is aligned.

10. An apparatus as defined in claim 9 wherein each ejection means is aligned with a plurality of detection units, and responds to output signals from each of the comparators associated with the plurality of detection units with which it is aligned.

* * * * *